(12) United States Patent
MacDougall et al.

(10) Patent No.: US 9,778,157 B2
(45) Date of Patent: Oct. 3, 2017

(54) OUTPUT MEMBER FOR A DIRECT IMPACT HOPKINSON PRESSURE BAR

(71) Applicant: ROLLS-ROYCE plc, London (GB)

(72) Inventors: Duncan Alexander Stuart MacDougall, Derby (GB); Kevin Anthony Brown, Nottingham (GB); Matthew David Jackson, Solihull (GB); Roger White, Shepperton (GB)

(73) Assignee: ROLLS-ROYCE plc, London (GB)

( * ) Notice: Subject to any disclaimer, the term of this patent is extended or adjusted under 35 U.S.C. 154(b) by 133 days.

(21) Appl. No.: 14/967,887

(22) Filed: Dec. 14, 2015

(65) Prior Publication Data
US 2016/0178496 A1 Jun. 23, 2016

(30) Foreign Application Priority Data
Dec. 22, 2014 (GB) .................................. 1422940.5

(51) Int. Cl.
| | | |
|---|---|---|
| G01N 3/30 | (2006.01) | |
| G01N 3/32 | (2006.01) | |
| G01N 3/00 | (2006.01) | |
| G01M 7/00 | (2006.01) | |
| G01N 3/307 | (2006.01) | |

(52) U.S. Cl.
CPC ............... *G01N 3/30* (2013.01); *G01N 3/307* (2013.01); *G01N 2203/0055* (2013.01); *G01N 2203/0098* (2013.01); *G01N 2203/0441* (2013.01)

(58) Field of Classification Search
None
See application file for complete search history.

(56) References Cited

U.S. PATENT DOCUMENTS

| | | | | |
|---|---|---|---|---|
| 4,696,182 A | * | 9/1987 | Meir | ...................... G01N 3/307 |
| | | | | 73/12.05 |
| 5,449,193 A | * | 9/1995 | Rivard | ............... B60G 21/0551 |
| | | | | 280/124.152 |
| 6,109,112 A | * | 8/2000 | Borza | ..................... F41H 11/12 |
| | | | | 73/661 |

(Continued)

FOREIGN PATENT DOCUMENTS

| | | |
|---|---|---|
| CN | 102680338 A | 9/2012 |
| CN | 202676558 U | 1/2013 |

(Continued)

OTHER PUBLICATIONS

Jun. 17, 2015 Search Report issued in British Patent Application No. GB1422940.5.

*Primary Examiner* — Peter Macchiarolo
*Assistant Examiner* — Jermaine Jenkins
(74) *Attorney, Agent, or Firm* — Oliff PLC

(57) ABSTRACT

An output member for a Direct Impact Hopkinson pressure bar includes an elongate tube portion and a disc-shaped cap portion. The tube portion has a first end and an opposite second end, while the cap portion includes a first face and an opposite second face. A circular stub protrudes from a center of the first face, and a circular cavity is formed in the second face. Each of the stub and the cavity is concentric with the cap portion, with a diameter of the cavity being greater than a diameter of the stub. The second face of the cap portion is positioned in intimate contact with the first end of the tube portion, with the cap portion being concentric with the tube portion.

16 Claims, 1 Drawing Sheet

(56) References Cited

U.S. PATENT DOCUMENTS

| | | | | |
|---|---|---|---|---|
| 6,116,077 | A | * 9/2000 | Albertini | G01N 3/30 |
| | | | | 73/12.05 |
| 7,533,557 | B1 | * 5/2009 | Mott | G01N 3/303 |
| | | | | 73/12.14 |
| 2016/0136993 | A1 | * 5/2016 | Kageyama | A45D 40/20 |
| | | | | 401/143 |

FOREIGN PATENT DOCUMENTS

| | | |
|---|---|---|
| CN | 203191250 U | 9/2013 |
| CN | 203643279 U | 6/2014 |

* cited by examiner

OUTPUT MEMBER FOR A DIRECT IMPACT HOPKINSON PRESSURE BAR

This disclosure claims the benefit of UK Patent Application No. GB1422940.5, filed on 22 Dec. 2014, which is hereby incorporated herein in its entirety.

FIELD OF THE DISCLOSURE

The present disclosure relates to an output member for a Direct Impact Hopkinson pressure bar.

BACKGROUND TO THE DISCLOSURE

A Split Hopkinson pressure bar is a mechanical test instrument that is used to characterise the dynamic response of materials when subjected to high strain rates.

FIG. 1 shows a schematic arrangement of a conventional Split Hopkinson pressure bar. A striker bar 10 is projected towards, and impacts against, a first end of the incident bar 12. Typical impact velocities range from 10 m/s to 20 m/s. This impact creates a stress wave that propagates along the incident bar towards the test specimen 14 that is positioned between the opposite second end of the incident bar 12 and a first end of the transmission bar 16.

When the stress wave reaches the test specimen 14 it splits into two smaller stress waves. The first of these smaller stress waves is transmitted through the test specimen 14 and into the transmission bar 16. The second of these smaller stress waves is reflected away from the test specimen 14 and back along the incident bar 12.

A stop bar 18 is provided at the second end of the transmission bar 16 to absorb the impact of the transmission bar 16.

Strain gauges are used at the incident bar 12 and the transmission bar 16 to record the stress waves.

A known problem with the Hopkinson pressure bar apparatus is that at impacting velocities above 20 m/s, the stresses generated in the incident and transmission bars may damage the bars themselves or the associated strain gauges.

One solution to this problem is to remove the incident bar and directly impact the test specimen with the striker bar. However, this arrangement, known as the Direct Impact Hopkinson bar, requires the use of high speed photography in the absence of the incident bar's strain gauge data. This increases the cost and complexity of such high strain rate testing.

Furthermore, once the test specimen is fully compacted, the impact loading may damage the transmission bar.

STATEMENTS OF DISCLOSURE

According to a first aspect of the present disclosure there is provided an output member for a Direct Impact Hopkinson pressure bar, comprising:
  an elongate tube portion comprising a first end and an opposite second end; and
  a disc-shaped cap portion comprising a first face and an opposite second face,
  wherein a circular stub protrudes from a center of the first face, a circular cavity is formed in the second face, each of the stub and the cavity being concentric with the cap portion, a diameter of the cavity being greater than a diameter of the stub, and the second face of the cap portion being positioned in intimate contact with the first end of the tube portion, with the cap portion being concentric with the tube portion.

The output member of the disclosure allows high strain rate loading of a test specimen or structure at a near constant strain rate until the applied load reaches a critical level. At this point the cap portion fails in plastic shear, with the circular stub shearing away from the body of the cap portion.

The disc-shaped cap portion therefore functions as a mechanical fuse to protect the transmission bar and its associated strain gauges from damage resulting from excessively high impact loads.

Optionally, the diameter of the stub is between 0.8 and 0.95 of the diameter of the cavity.

Optionally, the diameter of the stub is approximately 0.9 of the diameter of the cavity.

In one arrangement, the diameter of the stub is 70 mm and the diameter of the cavity is 75 mm.

Optionally, the cap portion further comprises an axial length being defined between the first face and the second face, and a depth of the circular cavity is between 6 mm and 12 mm less than the axial length.

The difference between the axial length of the cap portion and the depth of the circular cavity defines an axial length of a shear zone. Under pure shear loading, the load required to plastically deform this shear zone region will increase linearly with the axial length of the shear zone.

The axial length of this shear zone provides the cap portion with a particular value at which the circular stub shears away from the body of the cap portion. In other words, this ratio enables the 'fuse' function of the cap portion to be tailored to a particular testing application.

The shear zone is an annular ring of material extending axially from the first face of the cap portion to the distal face (i.e. the bottom) of the circular cavity, and extending radially from the outer diameter of the circular stub to the inner diameter of the circular cavity.

The aspect ratio of this shear zone can be varied to produce different failure displacement characteristics. For example, the ratio of the axial length of the shear zone to the radial width of the shear zone, i.e. the aspect ratio of the shear zone, may be between approximately 2:1 and 4:1. In one particular arrangement, the aspect ratio of the shear zone may be approximately 3:1.

Optionally, a distal surface of the circular stub is faced with a facing layer.

The use of a separate facing layer on the distal surface of the circular stub makes the axial surface harder and prevents localised crushing of its surface.

Optionally, the facing layer is formed from a material selected from the group comprising steels and titanium alloys.

Forming the facing layer from steel or a titanium alloy makes the cap portion more resistant to local plastic deformation during the impact process. This minimises the losses in the transfer of the stress wave from the test specimen to the output member.

Optionally, the cap portion is formed from a material selected from the group comprising aluminum alloys and magnesium alloys.

By forming the cap portion from an aluminum alloy it is possible to exploit the shear localization behavior of aluminum alloys. This makes the shear failure at the shear zone more repeatable and so makes the output member more effective as a mechanical fuse.

Optionally, the elongate tube portion comprises an internal cushion at the second end.

When the cap portion fails in plastic shear, the circular stub together with the test specimen are projected through the center of the cap portion. At this stage, the circular stub and the test specimen may still have considerable kinetic energy. In order to minimize any damage to these parts it is necessary to cushion their impact with the end of the transmission bar.

The internal cushion is a replaceable item that will absorb the energy resulting from the impact of the circular stub and the test specimen at the end of the transmission bar. This reduces the amount of remedial work required in the event of a failure of the cap portion.

In one arrangement, the internal cushion comprises Kevlar matting that is wadded into the first end of the elongate tube portion.

According to a second aspect of the present disclosure there is provided a Direct Impact Hopkinson pressure bar comprising an output member according to the first aspect of the disclosure.

Other aspects of the disclosure provide devices, methods and systems which include and/or implement some or all of the actions described herein. The illustrative aspects of the disclosure are designed to solve one or more of the problems herein described and/or one or more other problems not discussed.

BRIEF DESCRIPTION OF THE DRAWINGS

There now follows a description of an embodiment of the disclosure, by way of non-limiting example, with reference being made to the accompanying drawings in which.

It is noted that the drawings may not be to scale. The drawings are intended to depict only typical aspects of the disclosure, and therefore should not be considered as limiting the scope of the disclosure. In the drawings, like numbering represents like elements between the drawings.

DETAILED DESCRIPTION

Figure 1:
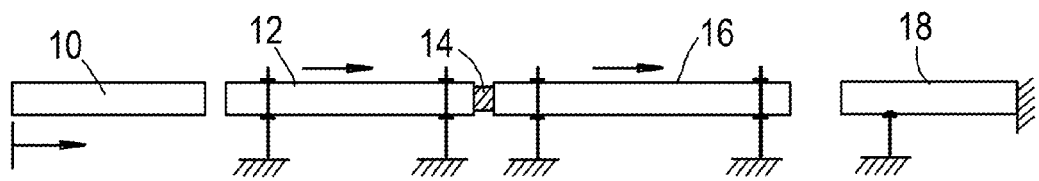
FIG. 1 shows a schematic elevational view of a Direct Impact Hopkinson pressure bar according to the prior art.
Figure 2:
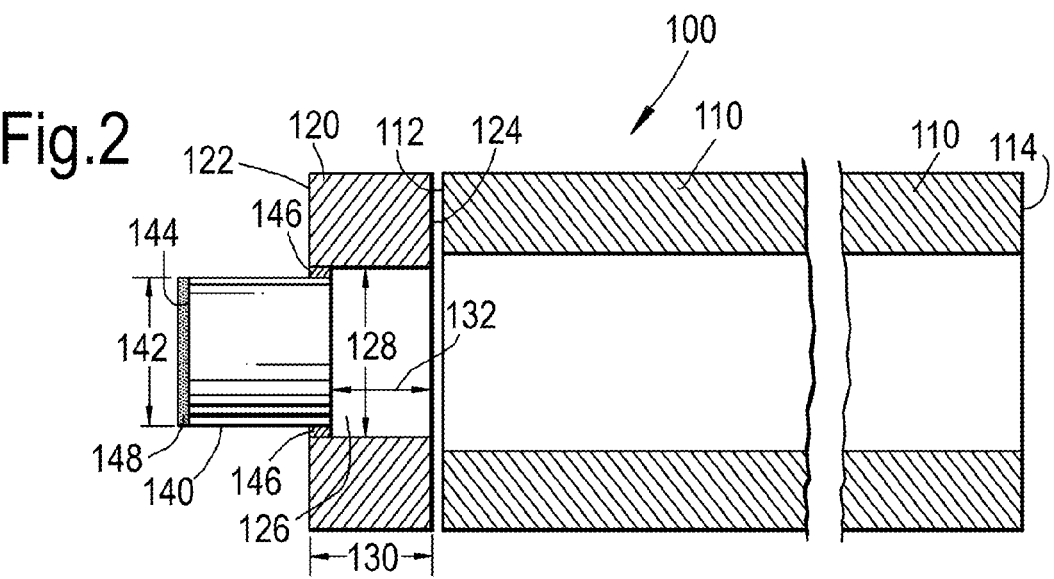
FIG. 2 shows a schematic partial sectional view of an output tube according to a first embodiment of the disclosure.
Figure 3:
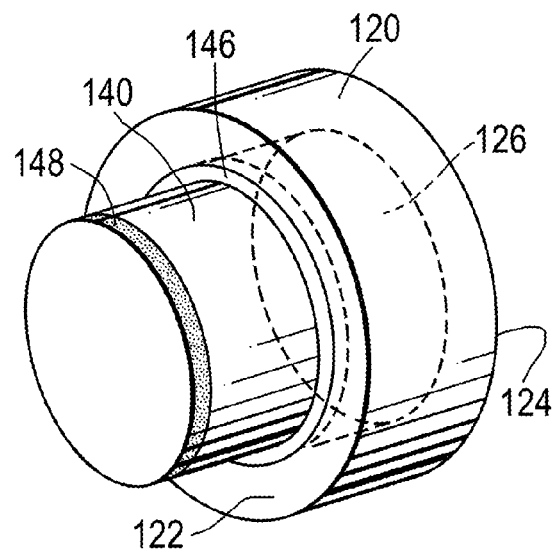
FIG. 3 shows a schematic, perspective view of the cap portion of the output member of FIG. 2.

Referring to FIGS. 2 and 3, an output member for a Direct Impact Hopkinson pressure bar according to a first embodiment of the disclosure is designated generally by the reference numeral 100.

The output member 100 comprises an elongate tube portion 110 and a disc-shaped cap portion 120. The tube portion 110 has a first end 112 and an opposite second end 114.

The cap portion 120 has a first face 122, an opposite second face 124, and an axial length 130. The axial length 130 extends between the first face 122 and the second face 124.

A circular stub 140 protrudes from a center of the first face 122 of the cap portion 120. A circular cavity is formed in the second face 124 of the cap portion 120. Each of the circular stub 140 and the circular cavity 126 is concentric with the cap portion 120.

A diameter 128 of the circular cavity 126 is greater than a diameter 142 of the circular stub 140. In the present arrangement, the diameter 142 of the circular stub 140 is 0.9 times the diameter 128 of the circular cavity 126. In other arrangements the ratio between the diameter 142 of the circular stub 140 and the diameter 128 of the circular cavity 126 may be between 0.8 and 0.95, with the proviso that the diameter 128 of the circular cavity 126 is always greater than the diameter 142 of the circular stub 140.

The axial length 130 of the cap portion 120 is greater than the depth 132 of the circular cavity 126 by a distance of 10 mm.

This geometry defines a shear zone 146 between the circular stub 140 and the cap portion 120. In other words, the shear zone is an annular ring of material extending axially from the first face of the cap portion to the distal face (i.e. the bottom) of the circular cavity, and extending radially from the outer diameter of the circular stub to the inner diameter of the circular cavity.

The shear zone can be defined by a shear zone aspect ratio; this being the ratio of the axial length of the shear zone to the radial width of the shear zone.

In the present embodiment, the shear zone has a radial width of 2.5 mm and an axial thickness of 7 mm. This provides a shear zone aspect ratio of 2.8.

In the present arrangement, the cap portion 120 is formed from an aluminum alloy. In an alternative arrangement, the cap portion 120 may be formed from a magnesium alloy.

The distal surface 144 of the circular stub 140 is provided with a facing layer 148. The facing layer 148 is formed from a high strength steel. In an alternative arrangement, the facing layer 148 may be formed from a titanium alloy.

In use, the cap portion 120 is positioned at the first end 112 of the tube portion 110 to together form the output member 100. The cap portion 120 is concentric with the tube portion 110. The output member 100 is then installed in a Direct Impact Hopkinson pressure bar apparatus with the apparatus being used in the conventional manner.

The foregoing description of various aspects of the disclosure has been presented for purposes of illustration and description. It is not intended to be exhaustive or to limit the disclosure to the precise form disclosed, and obviously, many modifications and variations are possible. Such modifications and variations that may be apparent to a person of skill in the art are included within the scope of the disclosure as defined by the accompanying claims.

What is claimed is:

1. An output member for a Direct Impact Hopkinson pressure bar, comprising:
    an elongate tube portion comprising a first end and an opposite second end; and
    a disc-shaped cap portion comprising a first face and an opposite second face,
    wherein a circular stub protrudes from a center of the first face, a circular cavity is formed in the second face, each of the stub and the cavity being concentric with the cap portion, a diameter of the cavity being greater than a diameter of the stub, and the second face of the cap portion being positioned in intimate contact with the first end of the tube portion, with the cap portion being concentric with the tube portion.

2. The output member as claimed in claim 1, wherein the diameter of the stub is between 0.8 and 0.95 of the diameter of the cavity.

3. A Direct Impact Hopkinson pressure bar comprising an output member as claimed in claim 2.

4. The output member as claimed in claim 1, wherein the diameter of the stub is approximately 0.9 of the diameter of the cavity.

5. A Direct Impact Hopkinson pressure bar comprising an output member as claimed in claim 4.

6. The output member as claimed in claim 1, the cap portion further comprising an axial length being defined between the first face and the second face, wherein a depth of the circular cavity is between 6 mm and 12 mm less than the axial length.

7. A Direct Impact Hopkinson pressure bar comprising an output member as claimed in claim 6.

8. The output member as claimed in claim 1, wherein a distal surface of the circular stub is faced with a facing layer.

9. A Direct Impact Hopkinson pressure bar comprising an output member as claimed in claim 8.

10. The output member as claimed in claim 8, wherein the facing layer is formed from a material selected from the group comprising steels and titanium alloys.

11. A Direct Impact Hopkinson pressure bar comprising an output member as claimed in claim 10.

12. The output member as claimed in claim 1, wherein the cap portion is formed from a material selected from the group comprising aluminum alloys and magnesium alloys.

13. A Direct Impact Hopkinson pressure bar comprising an output member as claimed in claim 12.

14. The output member as claimed in claim 1, wherein the elongate tube portion comprises an internal cushion at the second end.

15. A Direct Impact Hopkinson pressure bar comprising an output member as claimed in claim 14.

16. A Direct Impact Hopkinson pressure bar comprising an output member as claimed in claim 1.

* * * * *